(12) United States Patent
Lee et al.

(10) Patent No.: US 12,263,479 B2
(45) Date of Patent: Apr. 1, 2025

(54) ARRAY MICROFLUIDIC CHIP AND METHOD OF ANTIBIOTIC SUSCEPTIBILITY TESTING

(71) Applicant: MEDFLUID CO., LTD., Taipei (TW)

(72) Inventors: Wen-Bin Lee, Kaohsiung (TW); Shu-Hsien Liao, New Taipei (TW)

(73) Assignee: MEDFLUID CO., LTD., Taipei (TW)

( * ) Notice: Subject to any disclaimer, the term of this patent is extended or adjusted under 35 U.S.C. 154(b) by 854 days.

(21) Appl. No.: 17/490,014

(22) Filed: Sep. 30, 2021

(65) Prior Publication Data

US 2022/0314222 A1 Oct. 6, 2022

(30) Foreign Application Priority Data

Apr. 6, 2021 (TW) .................. 110112449

(51) Int. Cl.
*B01L 3/00* (2006.01)
*G01N 33/50* (2006.01)

(52) U.S. Cl.
CPC .... *B01L 3/502723* (2013.01); *G01N 33/5008* (2013.01); *B01L 2200/0684* (2013.01); *B01L 2200/0689* (2013.01); *B01L 2300/0819* (2013.01); *B01L 2300/0867* (2013.01); *B01L 2300/0887* (2013.01); *B01L 2300/161* (2013.01)

(58) Field of Classification Search
CPC ....... B01L 3/502723; B01L 2200/0684; B01L 2200/0689; B01L 2300/0819; B01L 2300/0867; B01L 2300/0887; B01L 2300/161; B01L 2300/0851; B01L 2300/0864; G01N 33/5008
See application file for complete search history.

(56) References Cited

U.S. PATENT DOCUMENTS

2020/0230597 A1* 7/2020 Lee ................. G01N 35/00584
2021/0079331 A1 3/2021 Chiou et al.

FOREIGN PATENT DOCUMENTS

| CN | 105289763 A | 2/2016 |
|---|---|---|
| CN | 107603866 A | 1/2018 |
| CN | 107643411 A | 1/2018 |
| CN | 108993621 A | 12/2018 |
| CN | 111632633 A | 9/2020 |
| CN | 111662804 A | 9/2020 |
| CN | 112500999 A | 3/2021 |
| WO | 9008196 A1 | 7/1990 |

* cited by examiner

*Primary Examiner* — Dennis White
(74) *Attorney, Agent, or Firm* — The Webb Law Firm

(57) ABSTRACT

An array microfluidic chip includes a chip mainbody, a transparent hydrophilic membrane, and a covering sheet. The chip mainbody includes a sample loading well and a plurality of reaction wells. The reaction wells are respectively connected to the sample loading well and arranged in an array form. The transparent hydrophilic membrane is disposed on the chip mainbody and covers the reaction wells. The transparent hydrophilic membrane includes a plurality of air pores and a first opening. The air pores are respectively connected to one of the reaction wells. The covering sheet covers the air pores and includes an adhesive element and a vent hole. The covering sheet, the adhesive element and the transparent hydrophilic membrane are stacked to form a vent space.

18 Claims, 12 Drawing Sheets
(2 of 12 Drawing Sheet(s) Filed in Color)

ARRAY MICROFLUIDIC CHIP AND METHOD OF ANTIBIOTIC SUSCEPTIBILITY TESTING

CROSS-REFERENCE TO RELATED APPLICATION

This application claims priority to Taiwanese Application Number 110112449 filed Apr. 6, 2021, the disclosure of which is hereby incorporated by reference in its entirety.

BACKGROUND OF THE INVENTION

Field of the Invention

The present disclosure relates to a microfluidic chip and a method of antibiotic susceptibility testing. More particularly, the present disclosure relates to a microfluidic chip including reaction wells arranged in an array form and a method of antibiotic susceptibility testing thereof.

Description of Related Art

In the modern society which is with highly developed medicine, the proper use of antibiotics is still an important aim for experts in the related arts so as to improve the treatment efficiency, reduce the production of drug-resistant strains and reduce the waste of medical resources.

The current protocols for antibiotic susceptibility testing include disk-diffusion test, minimum inhibitory concentration (MIC), minimum bactericidal concentration (MBC), checkboard test, time-kill curves test, and so on. However, the preparation of experiment materials and operation methods of the conventional antibiotic susceptibility testing are complicated and time-consuming, and the errors of the testing results may be generated from the differences in the operation, resulting in the accuracy and the efficiency of thereof being lower than expected.

Therefore, how to develop an antibiotic susceptibility testing platform, which is low-cost and with high stability so as to perform the antibiotic susceptibility testing rapidly and accurately and then provide more reliable test results for the use of antibiotics, has become the major aim in the related field of academia and industry.

SUMMARY OF THE INVENTION

According to one aspect of the present disclosure, an array microfluidic chip includes a chip mainbody, a transparent hydrophilic membrane and a covering sheet. The chip mainbody includes a sample loading well, a plurality of reaction wells and an independent well. The sample loading well is disposed on one side portion of the chip mainbody. The reaction wells are respectively pipe-connected to the sample loading well, wherein the reaction wells are arranged in an array form. The independent well is disposed separately from the sample loading well. The transparent hydrophilic membrane is disposed on the chip mainbody and covers the reaction wells, wherein the transparent hydrophilic membrane includes a plurality of air pores, a first opening and a second opening. The air pores are respectively connected to one of the reaction wells. The first opening is correspondingly connected to the sample loading well. The second opening is correspondingly connected to the independent well. The covering sheet is disposed on the transparent hydrophilic membrane and covers the air pores, wherein the covering sheet includes an adhesive element and a vent hole. The adhesive element is disposed on one surface of the covering sheet and is located between the covering sheet and the transparent hydrophilic membrane, wherein the adhesive element is arranged in a ring shape along an outer edge portion of the covering sheet. The covering sheet, the adhesive element and the transparent hydrophilic membrane are stacked to form a vent space, the vent space is connected to an external space of the array microfluidic chip through the vent hole, and the reaction wells are connected to the vent space through the air pores.

According to another aspect of the present disclosure, a method of antibiotic susceptibility testing includes following steps. An array microfluidic chip according to the aforementioned aspect is provided, wherein the array microfluidic chip is placed on an operating platform, and the reaction wells of the chip mainbody respectively store an antibiotic solution or a dried antibiotic powder. A bacterial solution adding step is performed, wherein the array microfluidic chip is placed tilted against the operating platform so as to make the side portion of the chip mainbody away from the operating platform, a bacteria-containing medium is added to the sample loading well from the first opening, and then the bacteria-containing medium is transported to each of the reaction wells from the sample loading well quantitatively. A sealing step is performed, wherein the first opening and the vent hole are sealed so as to isolate the sample loading well and the reaction wells from the external space of the array microfluidic chip. A mixing step is performed, wherein a relative position of the array microfluidic chip and the operating platform is adjusted so as to fully mix the bacteria-containing medium and the antibiotic solution or the dried antibiotic powder of each of the reaction wells and then form a reaction solution. A reacting step is performed, wherein the reaction solution is reacted for a predetermined reaction time so as to obtain a reaction result.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DESCRIPTION OF THE INVENTION

The present disclosure will be further exemplified by the following specific embodiments. However, the readers should understand that the present disclosure should not be limited to these practical details thereof, that is, in some embodiments, these practical details are used to describe how to implement the materials and methods of the present disclosure and are not necessary.

I. Array Microfluidic Chip of the Present Disclosure

Figure 1:
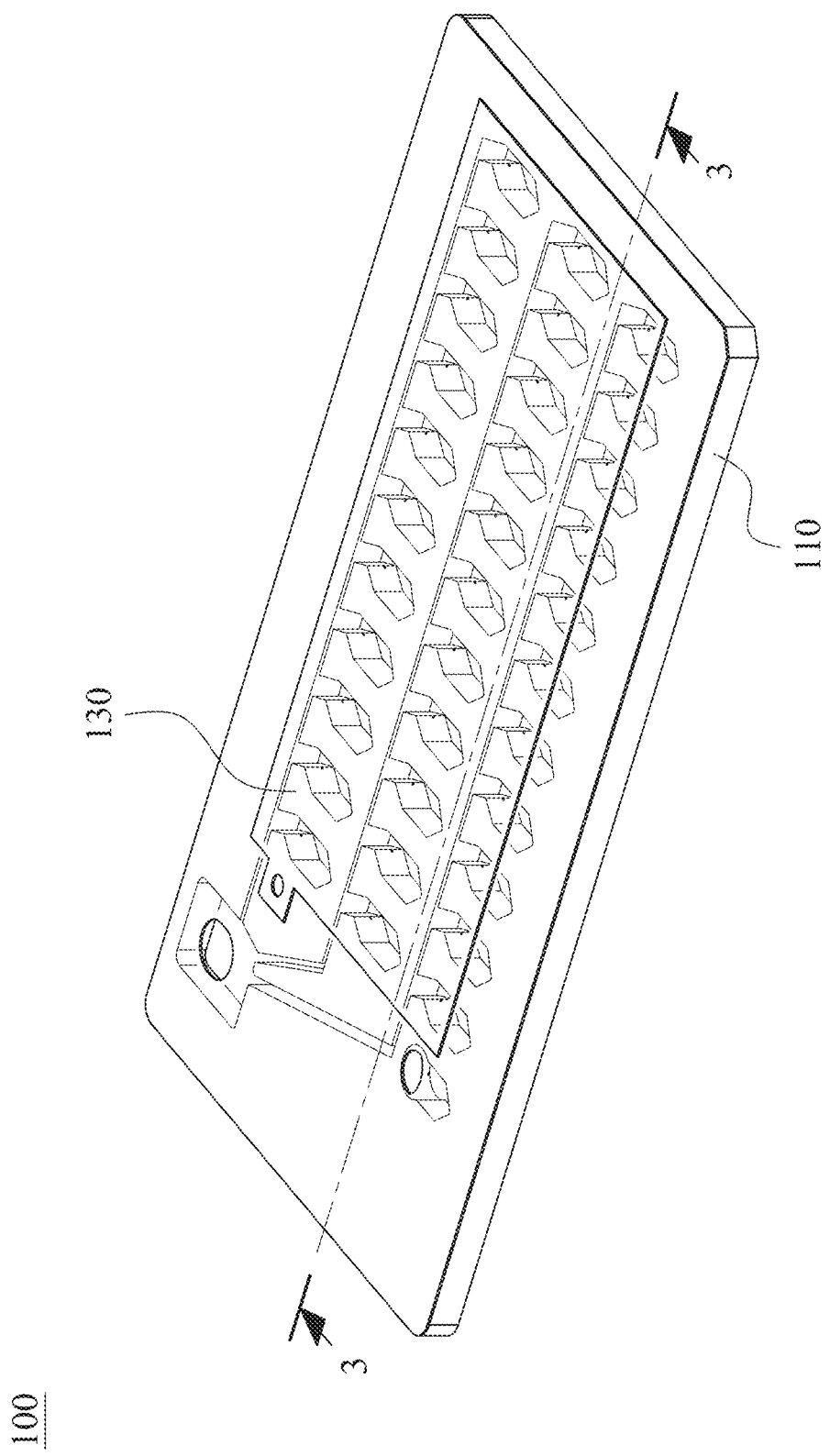
FIG. 1 is a schematic view of an array microfluidic chip according one embodiment of the present disclosure.
Figure 2:
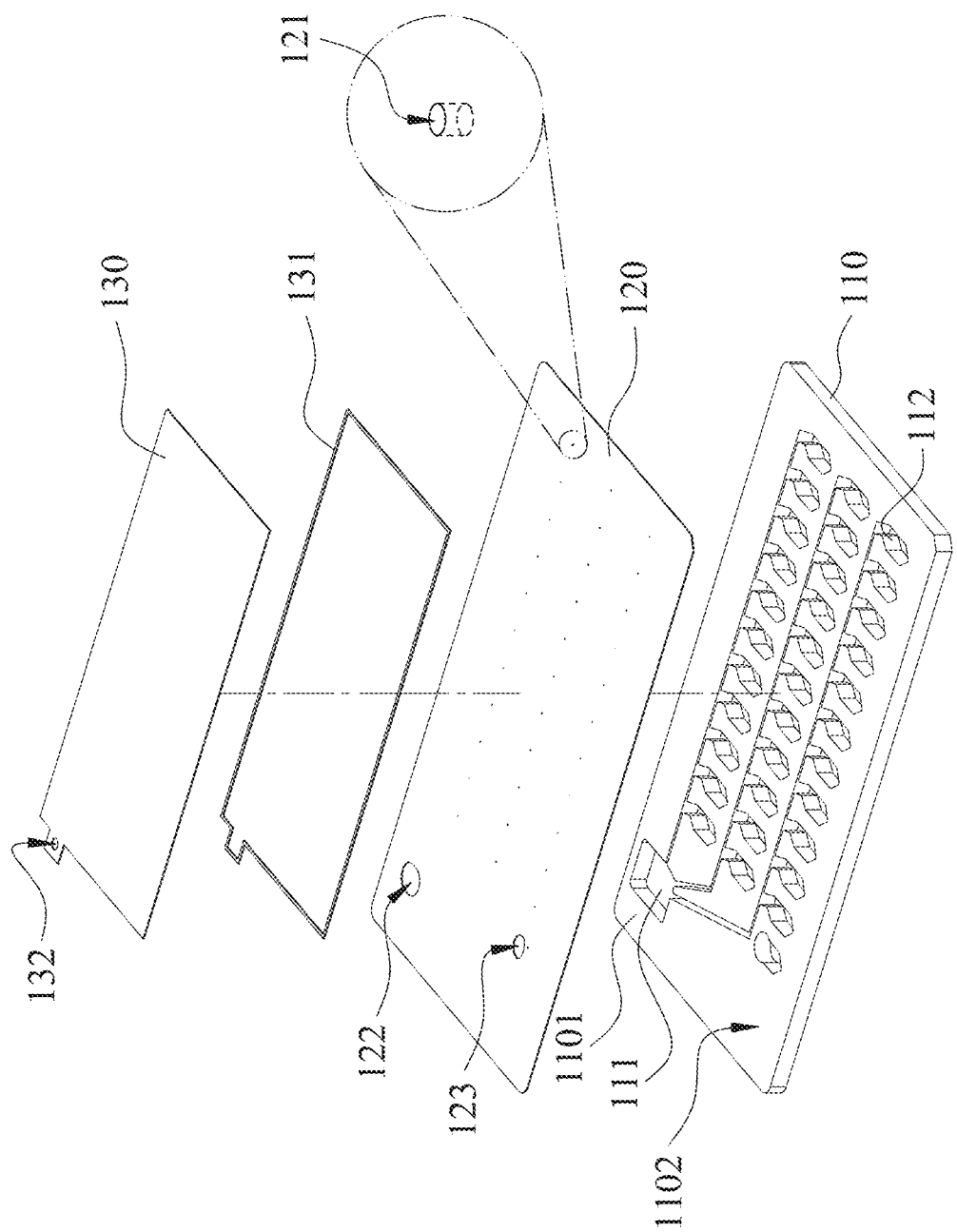
FIG. 2 is an exploded view of the array microfluidic chip of FIG. 1.
Figure 3:
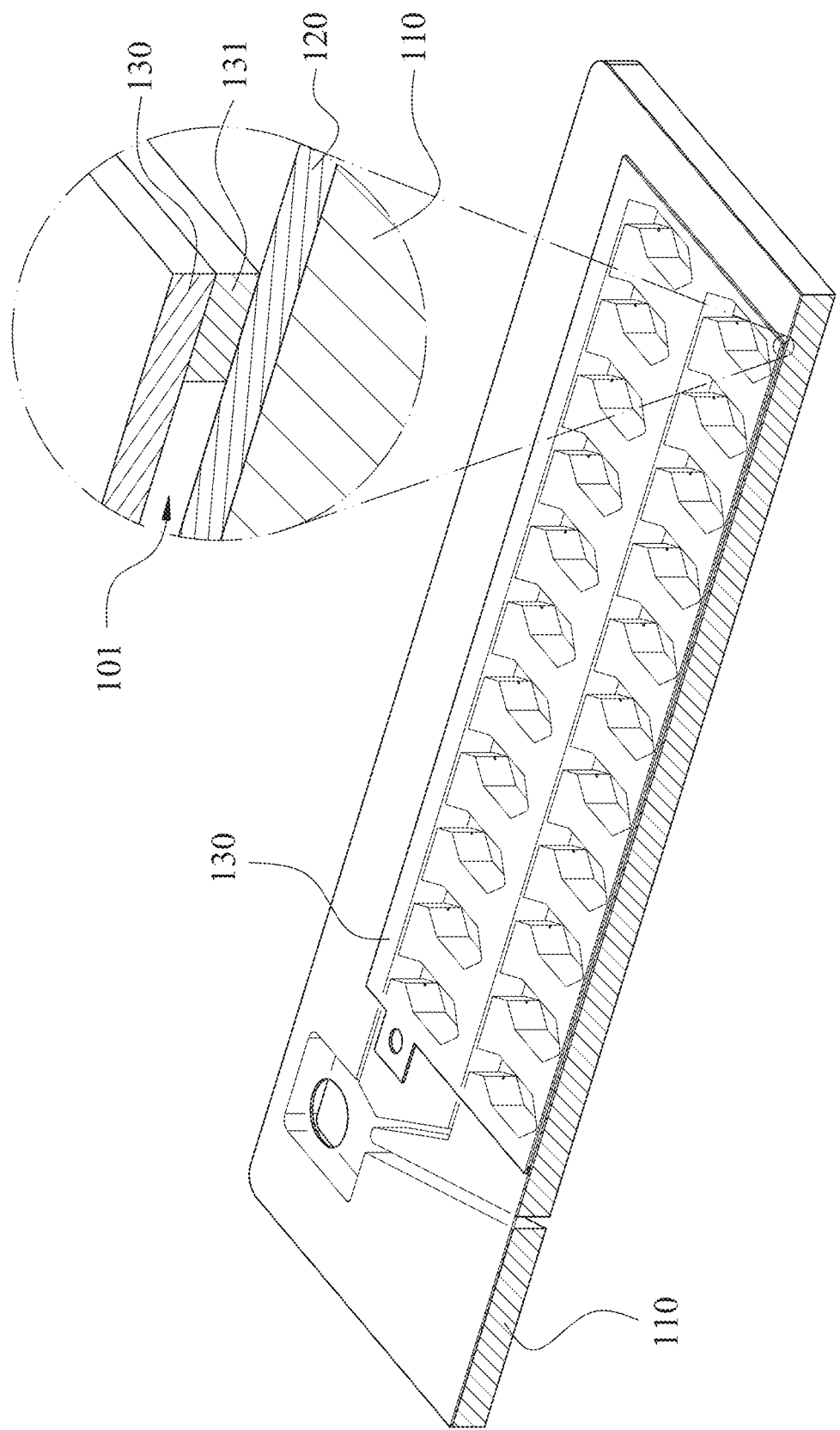
FIG. 3 is a cross-sectional view of the array microfluidic chip of FIG. 1 along Line 3-3.

Please refer to FIG. 1, FIG. 2 and FIG. 3, wherein FIG. 1 is a schematic view of an array microfluidic chip 100 according one embodiment of the present disclosure, FIG. 2 is an exploded view of the array microfluidic chip 100 of FIG. 1, and FIG. 3 is a cross-sectional view of the array microfluidic chip 100 of FIG. 1 along Line 3-3. The array microfluidic chip 100 includes a chip mainbody 110, a transparent hydrophilic membrane 120 and a covering sheet 130.

Figure 4:
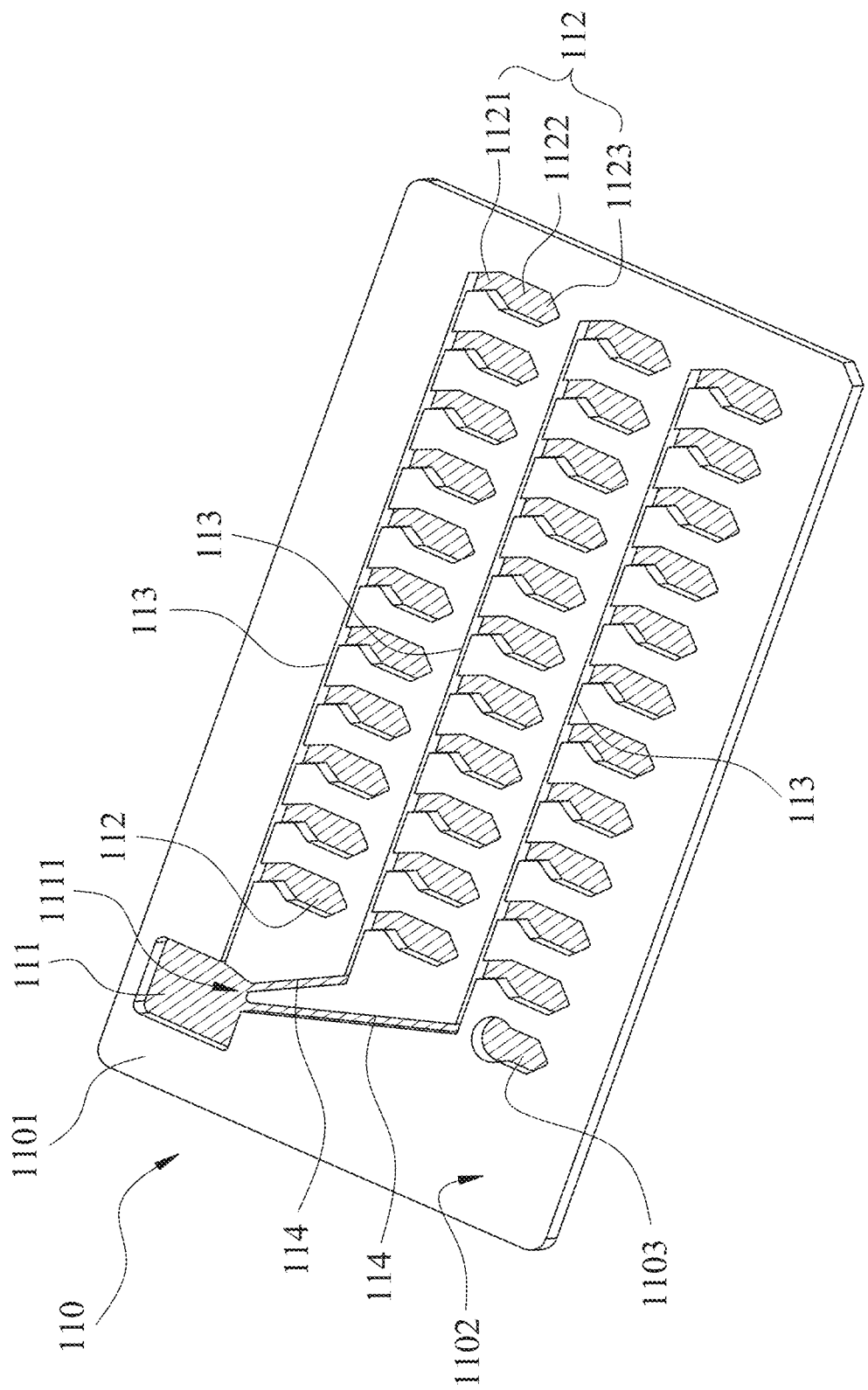
FIG. 4 is a schematic view of a chip mainbody of the array microfluidic chip of FIG. 1.

Please refer to FIG. 1, FIG. 2, FIG. 3 and FIG. 4 simultaneously, wherein FIG. 4 is a schematic view of a chip mainbody 110 of the array microfluidic chip 100 of FIG. 1. As shown in FIG. 1, FIG. 2, FIG. 3 and FIG. 4, the chip mainbody 110 includes a sample loading well 111 and a plurality of reaction wells 112. The sample loading well 111 is disposed on one side portion 1101 of the chip mainbody 110, the plurality of reaction wells 112 are respectively pipe-connected to the sample loading well 111, and the plurality of reaction wells 112 are arranged in an array form. Further, as shown in FIG. 4, the sample loading well 111 is disposed on the side portion 1101 which is located on a corner of the chip mainbody 110 being a rectangle, and the reaction wells 112 are disposed on other portions different from the side portion 1101 of the chip mainbody 110 in the array form. Therefore, it is favorable for respectively transporting the liquid added in the sample loading well 111 to the reaction wells 112, so that the use of the array microfluidic chip 100 of the present disclosure can be more convenient.

The transparent hydrophilic membrane 120 is disposed on the chip mainbody 110 and covers the reaction wells 112, and the transparent hydrophilic membrane 120 includes a plurality of air pores 121 and a first opening 122. The plurality of air pores 121 are respectively connected to one of the reaction wells 112, and the first opening 122 is correspondingly connected to the sample loading well 111. In detail, in the embodiment of FIG. 1, each of the reaction wells 112 corresponds to at least one of the air pores 121, and a diameter of each of the air pores 121 can range from 0.01 mm to 5 mm. Furthermore, the diameter of each of the air pores 121 can range from 0.5 mm to 1.5 mm, but the present disclosure is not limited thereto. Furthermore, a surface 1102 close to the transparent hydrophilic membrane 120 of the chip mainbody 110 can include an adhesive layer (not shown) so as to fix the transparent hydrophilic membrane 120 on the chip mainbody 110 and prevent the liquid from leaking from the reaction wells 112. Further, the adhesive layer can be made by proper adhesive materials according to actual needs, so that the aim of fixedly disposing of the transparent hydrophilic membrane 120 on the chip mainbody 110 can be achieved.

The covering sheet 130 is disposed on the transparent hydrophilic membrane 120 and covers the air pores 121, and the covering sheet 130 includes an adhesive element 131 and a vent hole 132. The adhesive element 131 is disposed on one surface (the reference number is omitted) of the covering sheet 130 and is located between the covering sheet 130 and the transparent hydrophilic membrane 120, and the adhesive element 131 is arranged in a ring shape along an outer edge portion (the reference number is omitted) of the covering sheet 130. As shown in FIG. 3, the covering sheet 130, the adhesive element 131 and the transparent hydrophilic membrane 120 are stacked to form a vent space 101, the vent space 101 is connected to an external space of the array microfluidic chip 100 (the reference number is omitted) through the vent hole 132, and the reaction wells 112 are respectively connected to the vent space 101 through one of the air pores 121. In detail, because the adhesive element 131 is disposed on the outer edge portion of the covering sheet 130 in the ring shape, the vent space 101 can be defined between the covering sheet 130 and the transparent hydrophilic membrane 120 when the covering sheet 130 and the transparent hydrophilic membrane 120 are stacked disposed, and each of the reaction wells 112 can be connected to the vent space 101 through the air pores 121. Thus, the liquid in the sample loading well 111 can be transported to each of the reaction wells 112 quantitatively by the adjustment of the air pores 121 corresponding to each of the reaction wells 112. Furthermore, the adhesive element 131 can be made of double-sided tape, acrylic glue, UV curable adhesive, or other adhesive materials, but the present disclosure is not limited thereto.

Figure 5:
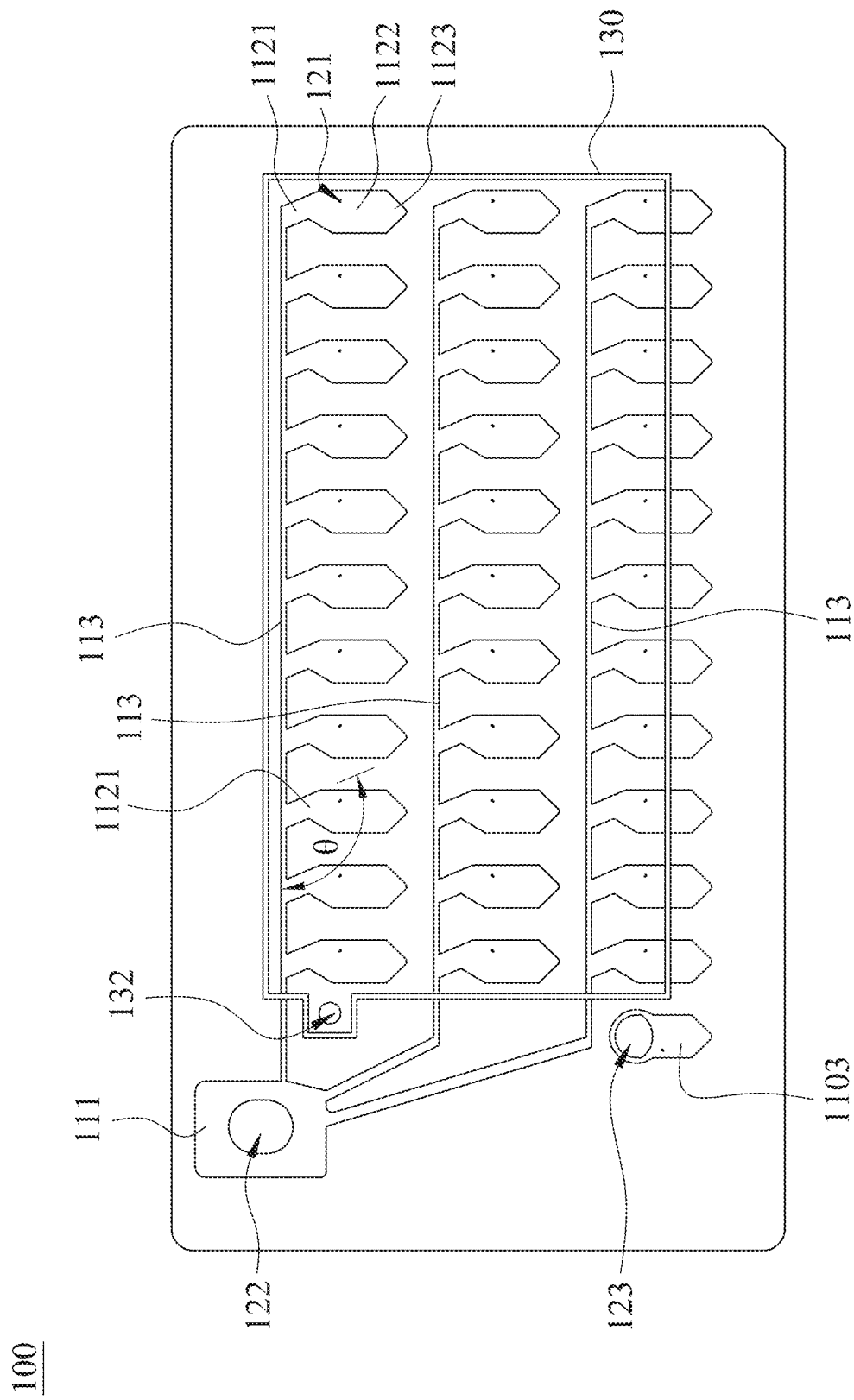
FIG. 5 is another schematic view of the array microfluidic chip of FIG. 1.

Please refer to FIG. 4 and FIG. 5 simultaneously, wherein FIG. 5 is another schematic view of the array microfluidic chip 100 of FIG. 1. As shown in FIG. 4 and FIG. 5, the chip mainbody 110 can further include a parallel flow channel 113, the sample loading well 111 can include a pipe-connected portion 1111, and the pipe-connected portion 1111 is disposed on one side of the sample loading well 111 away from the side portion 1101 of the chip mainbody 110. The parallel flow channel 113 is connected to the pipe-connected portion 1111, and each of the reaction wells 112 is connected to the parallel flow channel 113. Furthermore, a width of the parallel flow channel 113 can range from 0.02 mm to 5.0 mm. Furthermore, the width of the parallel flow channel 113 can range from 0.2 mm to 2.0 mm. Therefore, by the arrangement of the parallel flow channel 113 with the width in proper, the liquid added to the sample loading well 111 can fill in the area of the parallel flow channel 113 between two of the reaction wells 112 continuously after being transported to each of the reaction wells 112 quantitatively. Thus, liquid barriers will be formed between different reaction wells 112 by the liquid remaining in the parallel flow channel 113. Further, when the chip mainbody 110 is placed vertically, a gas-water isolation area will be formed between the reaction wells 112 so as to prevent the interference between different reaction wells 112 during operation.

As shown in FIG. 4 and FIG. 5, the chip mainbody 110 can further include at least one slanting flow channel 114, and a number of the parallel flow channel 113 is at least two. The slanting flow channel 114 is connected between one of the parallel flow channels 113 and the pipe-connected portion 1111, and the one of the parallel flow channels 113 is connected to the sample loading well 111 through the slanting flow channel 114. Therefore, by the arrangement that the parallel flow channel 113 is directly connected to the sample loading well 111, or indirectly connected to the sample loading well 111 through the slanting flow channel 114, the liquid added to the sample loading well 111 can be accumulated in the pipe-connected portion 1111 first. Further, when the pipe-connected portion 1111, the parallel flow channels 113 and the slanting flow channel 114 are filled with the liquid, the aforementioned liquid will be transported to the reaction wells 112, respectively. Accordingly, it is favorable for preventing the liquid volume transported to the reaction wells 112 from affecting by the bubbles existing in the parallel flow channel 113 and the slanting flow channel 114 and then further affecting the effects of the quantitative transportation. Furthermore, in the embodiment of FIG. 4, the number of the parallel flow channels 113 is three, and a number of the slanting flow channel 114 is two. One of the parallel flow channels 113 is directly connected to the pipe-connected portion 1111, the two slanting flow channels 114 are respectively connected to the other two parallel flow channels 113, and the other two parallel flow channels 113 are respectively connected to the sample loading well 111 through the two slanting flow channels 114. Moreover, it must be noted that the numbers of the parallel flow channels 113 and the slanting flow channels 114 are not limited to the drawings of the present disclosure.

Furthermore, as shown in FIG. 4 and FIG. 5, each of the reaction wells 112 includes a slanting chamber 1121 and a reaction chamber 1122. One end portion of the slanting chamber 1121 is connected to the parallel flow channel 113, and the reaction chamber 1122 is connected to the other end portion of the slanting chamber 1121. There is an angle θ between a long axis of the slanting chamber 1121 of each of the reaction wells 112 and the parallel flow channel 113, and the angle θ can range from 90° to 179°. Furthermore, the angle θ can range from 95° to 175°. Therefore, by the arrangement of the slanting chamber 1121, the liquid of the sample loading well 111 can be transported to each of the reaction wells 112 smoothly, so that the subsequent operation process of the antibiotic susceptibility testing can be simplified. Furthermore, a width of the slanting chamber 1121 of each of the reaction wells 112 can be larger than 0.1 mm. Furthermore, the width of the slanting chamber 1121 of each of the reaction wells 112 can be larger than 1 mm, but the present disclosure is not limited thereto.

Furthermore, in the embodiment of FIG. 4 and FIG. 5, each of the air pores 121 corresponds to the reaction chamber 1122 of one of the reaction wells 112. Based on the required volume of the liquid, the position of the air pore 121 can be arranged on the side of each of the reaction wells 112 close to slanting chamber 1121 (the required volume of the liquid is less), or on the side of each of the reaction wells 112 away from the slanting chamber 1121 (the required volume of the liquid is more). However, the present disclosure is not limited by the embodiments disclosed in the drawings.

Furthermore, as shown in FIG. 4 and FIG. 5, the reaction chamber 1122 of each of the reaction wells 112 includes a bottom portion 1123, and a shape of the bottom portion 1123 can be arc shape or acute-angle shape. Therefore, it is favorable for observing through the transparent hydrophilic membrane 120 the sedimentation of microorganisms in the reaction chambers 1122 after the array microfluidic chip 100 of the present disclosure is used to perform the antibiotic susceptibility testing or other tests. Thus, the use of the array microfluidic chip 100 of the present disclosure can be more convenient.

Furthermore, the chip mainbody 110, the transparent hydrophilic membrane 120 and the covering sheet 130 of the array microfluidic chip 100 of the present disclosure can be made of a plastic material, but the present disclosure is not limited thereto.

Furthermore, in the embodiment of FIG. 4 and FIG. 5, the chip mainbody 110 can further include an independent well 1103, and the transparent hydrophilic membrane 120 can further include a second opening 123. The independent well 1103 is disposed separately from the sample loading well 111, and the second opening 123 is correspondingly connected to the independent well 1103. The arrangement of the independent well 1103 can provide a well for performing a negative control test on the array microfluidic chip 100 of the present disclosure so as to compare with the testing result obtained from the reaction wells 112. Therefore, the breadth of application of the array microfluidic chip 100 of the present disclosure can be enhanced.

Therefore, by the arrangement of the plurality of reaction wells 112 which are arranged in the array form, the resistance tests of different drugs and the microbial cultivation can be performed at the same time on the array microfluidic chip 100 of the present disclosure, and the cross-contamination between the reaction wells 112 can be further prevented. Thus, the antibiotic susceptibility testing can be performed rapidly by using the array microfluidic chip 100 of the present disclosure under the premise that the mutual contaminations and interferences of reagents are prevented. Furthermore, by the arrangements that the plurality of air pores 121 are respectively connected to one of the reaction wells 112 and the reaction wells 112 are connected to the vent space 101 through the air pores 121, the samples added to sample loading well 111 can be transported to each of the reaction wells 112 quantitatively. Thus, the testing accuracy of the array microfluidic chip 100 of the present disclosure can be enhanced significantly and has application potentials in related markets. Moreover, by the arrangement of the parallel flow channel 113 with the width in proper a proper width, the liquid added to the sample loading well 111 can fill in the area of the parallel flow channel 113 between two of the reaction wells 112 continuously after being transported to each of the reaction wells 112 quantitatively. Further, when the chip mainbody 110 is placed vertically, a gas-water isolation area will be formed between the reaction wells 112. Accordingly, it is favorable for preventing the cross-contamination caused by sample backflow between different reaction wells 112 during operation.

II. Method of Antibiotic Susceptibility Testing of the Present Disclosure

Figure 6:
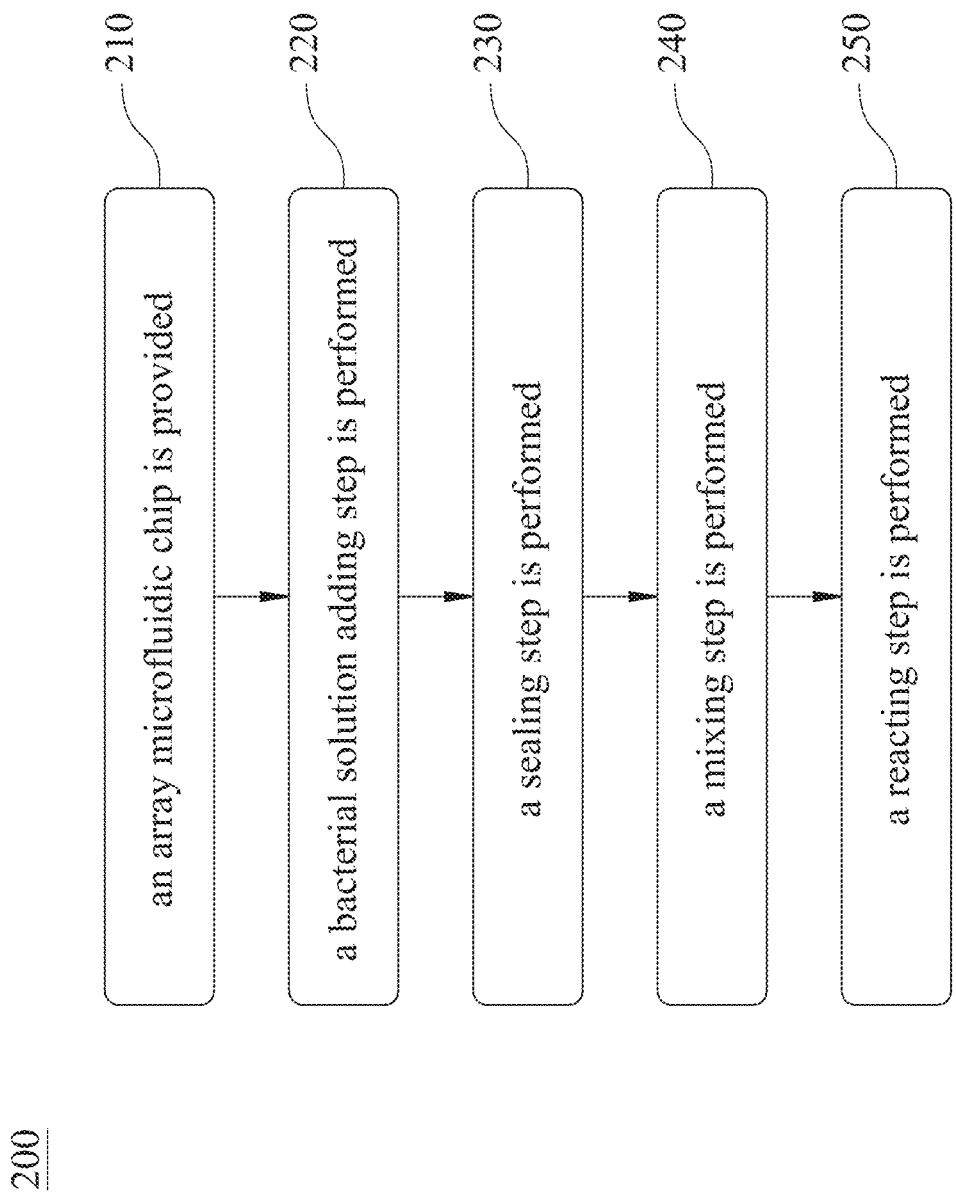
FIG. 6 is a flow chart of a method of antibiotic susceptibility testing according another embodiment of the present disclosure.
Figure 7A:
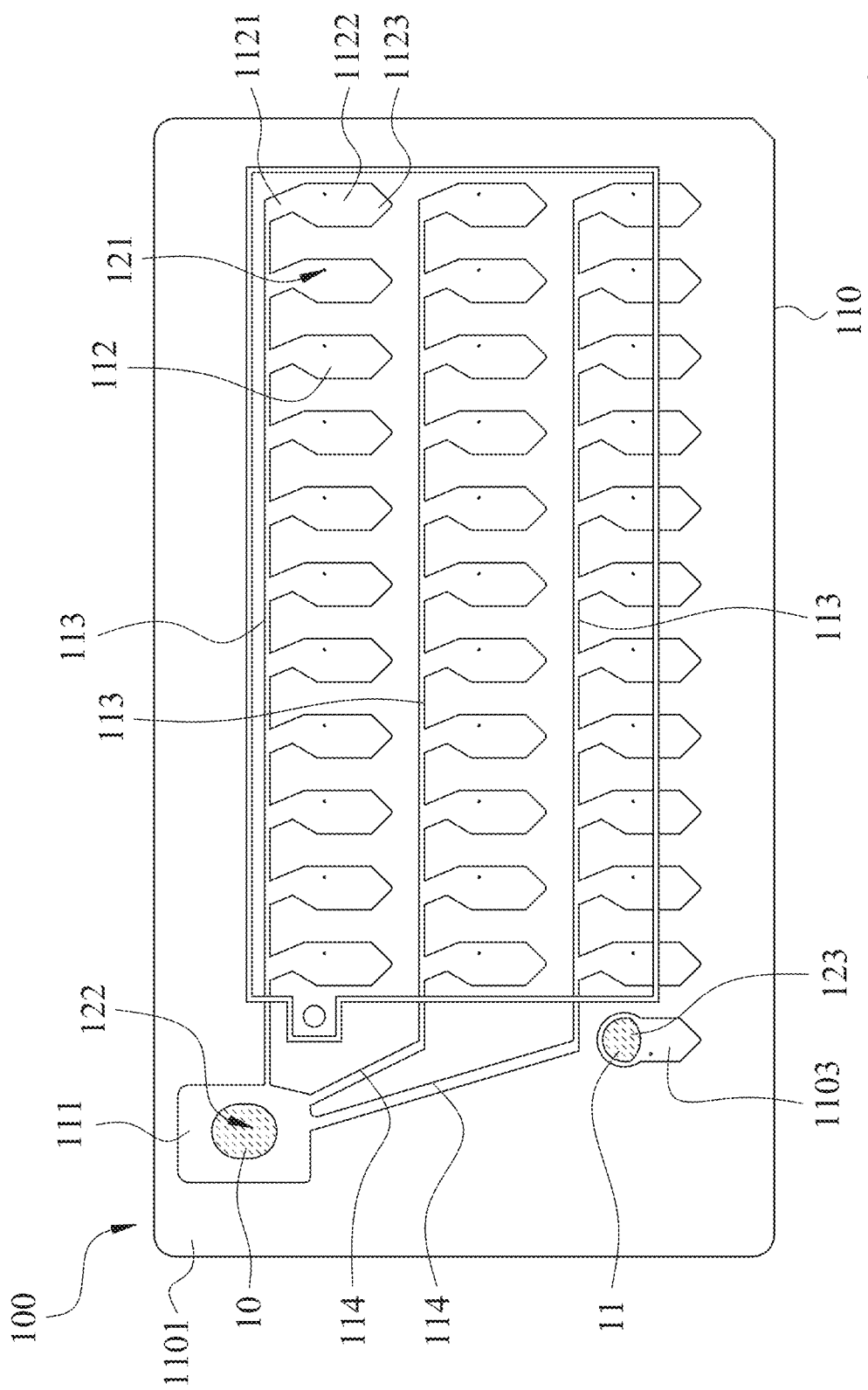
FIG. 7A is an operating schematic view of the method of antibiotic susceptibility testing of FIG. 6.
Figure 7B:
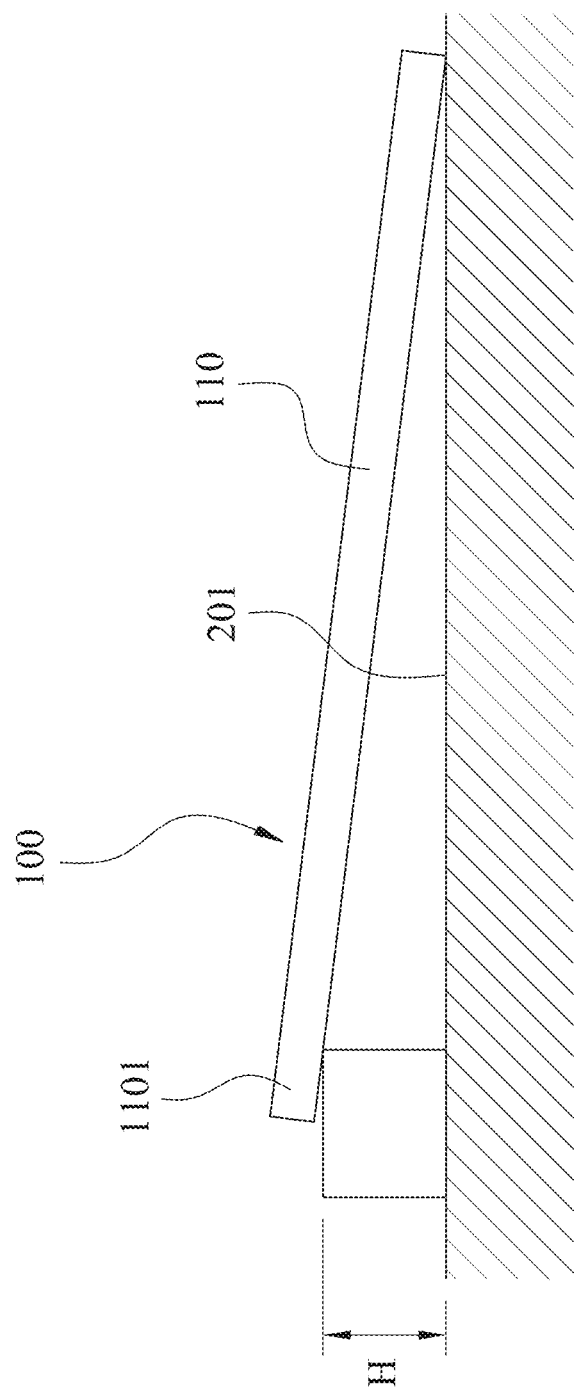
FIG. 7B is a schematic view of an array microfluidic chip which is placed tilted against an operating platform in the method of antibiotic susceptibility testing of FIG. 7A.
Figure 8:
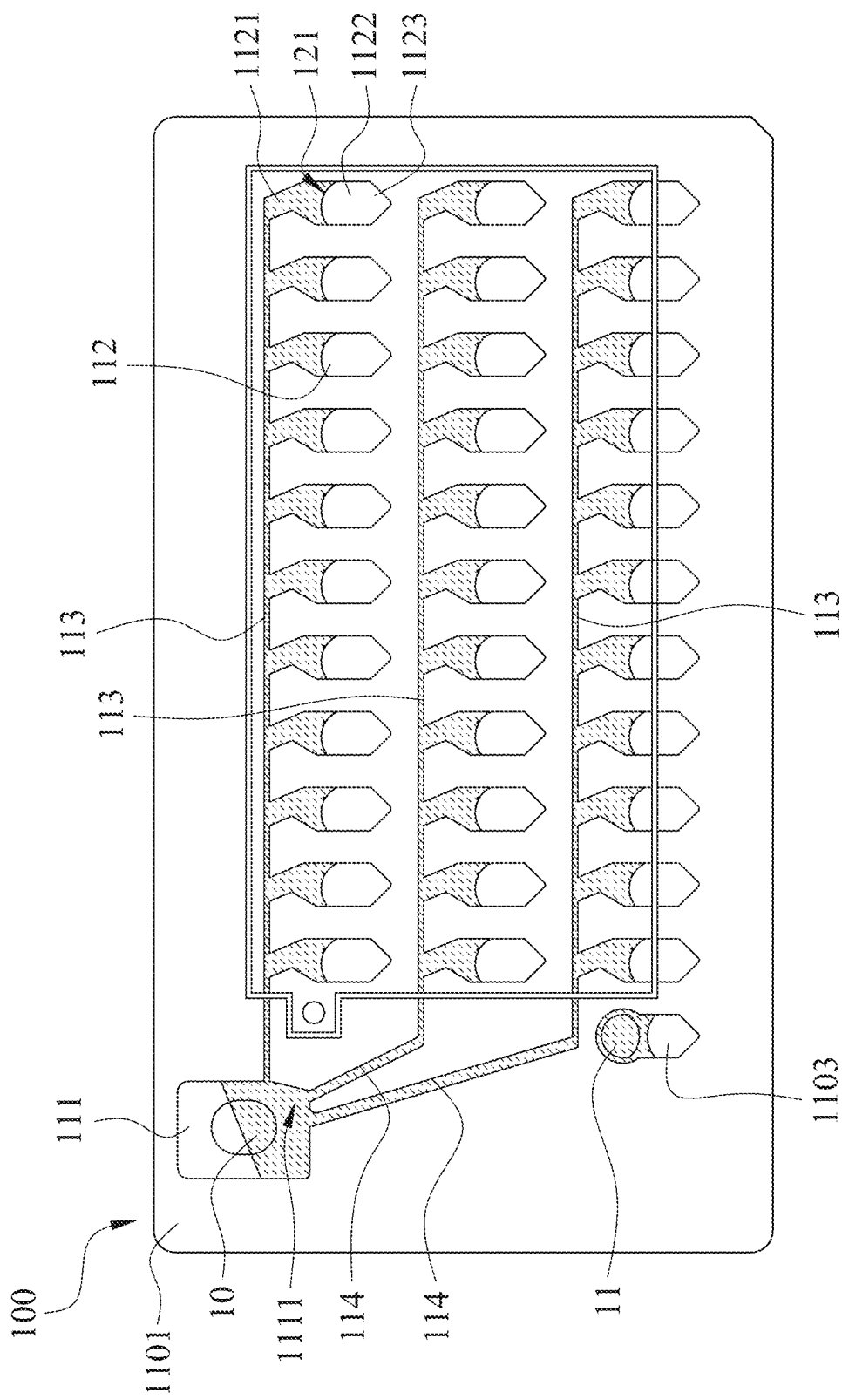
FIG. 8 is another operating schematic view of the method of antibiotic susceptibility testing of FIG. 6.
Figure 9:
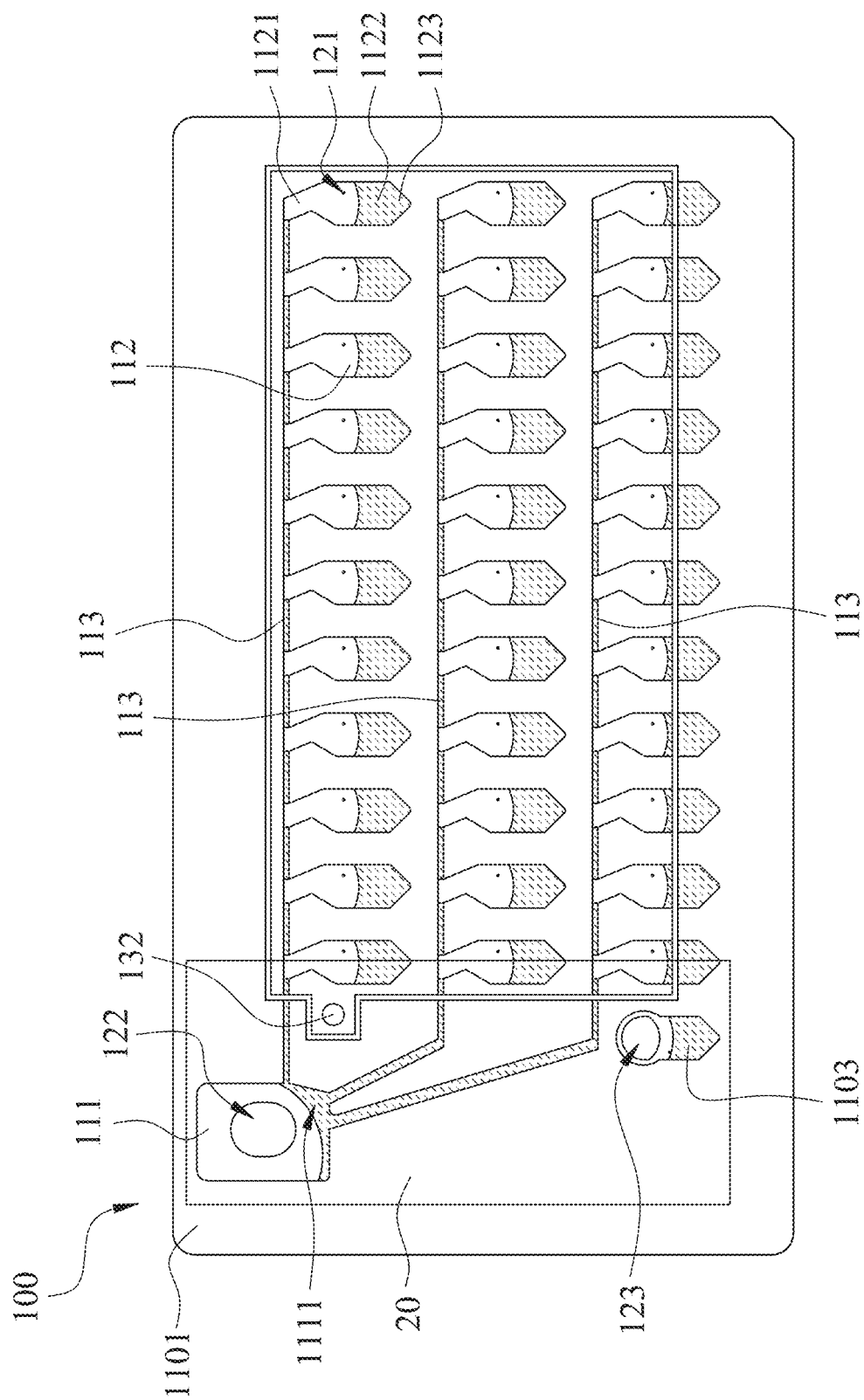
FIG. 9 is further another operating schematic view of the method of antibiotic susceptibility testing of FIG. 6.

Please refer to FIGS. 6, 7A, 7B, 8 and 9, wherein FIG. 6 is a flow chart of a method 200 of antibiotic susceptibility testing according another embodiment of the present disclosure, FIG. 7A is an operating schematic view of the method 200 of antibiotic susceptibility testing of FIG. 6, FIG. 7B is a schematic view of an array microfluidic chip 100 which is placed tilted against an operating platform 201 in the method 200 of antibiotic susceptibility testing of FIG. 7A, FIG. 8 is another operating schematic view of the method 200 of antibiotic susceptibility testing of FIG. 6, and FIG. 9 is further another operating schematic view of the method 200 of antibiotic susceptibility testing of FIG. 6. The details of the method 200 of antibiotic susceptibility testing of FIG. 6 will be further described accompanied by FIGS. 7A, 7B, 8 and 9, and the method 200 of antibiotic susceptibility testing of the present disclosure includes Step 210, Step 220, Step 230, Step 240 and Step 250.

In Step 210, an array microfluidic chip is provided. In detail, the method 200 of antibiotic susceptibility testing of the present disclosure is performed by the array microfluidic chip 100 of the present disclosure, and the structural details of the array microfluidic chip 100 of the present disclosure are described in the aforementioned description and do not described again herein. As shown in FIG. 7A and FIG. 7B, the array microfluidic chip 100 is placed on the operating platform 201, and the reaction wells 112 of the chip mainbody 110 respectively store an antibiotic solution or a dried antibiotic powder (not shown).

In Step 220, a bacterial solution adding step is performed. In detail, as shown in FIG. 7A, FIG. 7B and FIG. 8, the array microfluidic chip 100 is placed tilted against the operating platform 201 in Step 220 so as to make the side portion 1101 of the chip mainbody 110 away from the operating platform 201 (as shown in FIG. 7B), and then a bacteria-containing medium 10 is added to the sample loading well 111 from the first opening 122 (as shown in FIG. 7A). At this time, the bacteria-containing medium 10 is transported to each of the reaction wells 112 from the sample loading well 111 (as shown in FIG. 8), and the bacteria-containing medium 10 is transported to each of the reaction wells 112 from the sample loading well 111 quantitatively. In particular, a height of the side portion 1101 of the chip mainbody 110 away from the operating platform 201 is H, and the following condition is satisfied: H≥1 cm. Therefore, by the arrangement that the side portion 1101 is away from the operating platform 201, the bacteria-containing medium 10 will be further transported to each of the reaction wells 112 directly through the parallel flow channel 113 or sequentially through the slanting flow channel 114 and the parallel flow channel 113 from the sample loading well 111 due to the gravity.

As shown in FIG. 8, because the side portion 1101 is placed away from the operating platform 201, the bacteria-containing medium 10 of the sample loading well 111 will be accumulated in the pipe-connected portion 1111 which is away from the side portion 1101 of the chip mainbody 110 first. Further, when the pipe-connected portion 1111, the parallel flow channels 113 and the slanting flow channel 114 are filled with the liquid, the bacteria-containing medium 10 will be transport to the reaction wells 112, respectively. Accordingly, it is favorable for preventing the liquid volume transported to the reaction wells 112 from affecting by the bubbles existing in the parallel flow channel 113. Furthermore, because each of the reaction wells 112 is connected to the vent space 101 through the air pores 121 (please refer to FIG. 3), the introduction of the bacteria-containing medium 10 from the slanting chamber 1121 to the reaction chamber 1122 will be stopped at the position where the air pore 121 is located, and then a gas-water interface will be formed at the position of the air pore 121 as a boundary. Therefore, the volume of the bacteria-containing medium 10 transported to each of the reaction wells 112 can be adjusted based on the position of the air pores 121, so that the aim of quantitative transportation can be achieved.

Furthermore, as shown in FIG. 7A, in the bacterial solution adding step, a bacteria-free medium 11 will be further added to the independent well 1103 from the second opening 123 so as to establish a negative control test of the method 200 of antibiotic susceptibility testing. Therefore, the breadth of application of the method 200 of antibiotic susceptibility testing of the present disclosure can be enhanced.

In Step 230, a sealing step is performed, wherein the first opening 122 and the vent hole 132 are sealed so as to isolate the sample loading well 111 and the reaction wells 112 from the external space of the array microfluidic chip. As shown in FIG. 9, the sealing step is performed by the sealing film 20 or other materials that can seal the first opening 122 and the vent hole 132. Simultaneously, the second opening 123 will be sealed. Thus, it is favorable for facilitating the performance of the following mixing step.

In Step 240, a mixing step is performed, wherein a relative position of the array microfluidic chip 100 and the operating platform 201 is adjusted so as to fully mix the bacteria-containing medium 10 and the antibiotic solution or the dried antibiotic powder of each of the reaction wells 112 and then form a reaction solution. In detail, in the mixing step, the array microfluidic chip 100 will be placed on a culture rack in a manner that an long axis of each of the reaction wells 112 is perpendicular to the surface of the operating platform 201, or the long axis of the parallel flow channel 113 of the array microfluidic chip 100 will be perpendicular to the surface of the operating platform 201 by hand-held. Thus, the bacteria-containing medium 10 can fall and reach the bottom portion 1123 of the reaction chamber 1122 of each of the reaction wells 112 due to the gravity and then mix with the antibiotic solution or the dried antibiotic powder thereof so as to form the reaction solution for the following analysis.

In Step 250, a reacting step is performed, wherein the reaction solution is reacted for a predetermined reaction time so as to obtain a reaction result. In detail, the aforementioned predetermined reaction time is set according to different microorganisms and different antibiotics and can be 3 hours to 24 hours. Furthermore, in the reacting step, a cultivation status of the reaction solution culturing for the predetermined reaction time can be further analyzed so as to assess the reaction result of antibiotic susceptibility of the microorganism in the bacteria-containing medium 10 to the antibiotics.

Therefore, the method 200 of antibiotic susceptibility testing of the present disclosure is performed by using the array microfluidic chip 100 of the present disclosure, so that the operating steps of the conventional antibiotic susceptibility test can be simplified and the errors caused by the manual operation can be avoided. Thus, the testing accuracy of the method 200 of antibiotic susceptibility testing of the present disclosure can be enhanced significantly and has application potentials in related markets.

III. Assessing the Consistency of Fluid Volume Transferred by the Array Microfluidic Chip of the Present Disclosure The present test is performed by the array microfluidic chip 100 of FIG. 1 for assessing the consistency of fluid volume transferred with two repetitions, wherein the two array microfluidic chips 100 used in the test are renamed as the first array microfluidic chip and the second array microfluidic chip. It must be noted that the terms "first" and "second" are not used to describe a specific sequence thereof but to illustrate the two testing groups used the array microfluidic chips 100 with the same specifications. In detail, both of the first array microfluidic chip and the second array microfluidic chip include an upper array, a middle array and a lower array, the upper array, the middle array and the lower array respectively include 11 reaction wells. Further, the structural details of the first array microfluidic chip and the second array microfluidic chip are described in the aforementioned description and do not described again herein. The assessing steps of the consistency of volume fluid are similar with Step 210 to Step 230 of the method 200 of antibiotic susceptibility testing of the present disclosure, and the only difference there between is that the reaction wells of the chip mainbody in the present experiment are without the antibiotic solution, the dried antibiotic powders or other solutions. Furthermore, the aforementioned bacteria-containing medium is replaced with a bacteria-free medium so as to observe the difference of liquid volumes in each of the reaction wells of the first array microfluidic chip and the second array microfluidic chip in a single operation.

Please refer to Table 1, which shows the measuring results of the liquid volumes in the different reaction wells of the different array microfluidic chips (the unit of the liquid volumes is μL).

contents, and then the array microfluidic chip is sealed and keeps refrigerated. Next, redox indicators with proper amounts are respectively added to the bacteria-containing mediums including *E. coli* ATCC25922 or *S. aureus* ATCC29213, and the bacteria-containing mediums are transported to different reaction wells of different array microfluidic chips and then mixed with the antibiotic powders with different contents thereof so as to form the reaction solutions including different concentrations of antibiotics.

Next, the array microfluidic chips are placed in the incubator and cultured at 37° C., and the antibiotic susceptibilities of *E. coli* ATCC25922 and *S. aureus* ATCC29213 to Amikacin, Gentamicin and Vancomycin are further assessed based on the discoloration of the reaction solutions. In detail, if *E. coli* ATCC25922 and *S. aureus* ATCC29213 can grow under the existence of a specific antibiotic with a particular concentration, the color of the reaction solution including the redox indicator will gradually change from blue to purple, and eventually to pink, and the discoloration can be observed on the array microfluidic chip directly. Therefore, the assessing time of the method of antibiotic susceptibility testing of the present disclosure can be greatly shortened.

TABLE 1

| | First array microfluidic chip | | | | Second array microfluidic chip | | |
|---|---|---|---|---|---|---|---|
| Array | Upper | Middle | Lower | Array | Upper | Middle | Lower |
| 1 | 49.2 | 51.1 | 50.1 | 1 | 48.6 | 47 | 49.7 |
| 2 | 50.6 | 51.1 | 50.6 | 2 | 48.6 | 48.2 | 49.7 |
| 3 | 50.6 | 51.1 | 50.6 | 3 | 46.6 | 48.9 | 47.4 |
| 4 | 51.7 | 52.4 | 51.9 | 4 | 48.2 | 49.6 | 51.7 |
| 5 | 51.7 | 51.5 | 52.1 | 5 | 50.1 | 50.7 | 51.7 |
| 6 | 51.7 | 51.5 | 51.7 | 6 | 50.1 | 49.2 | 51.2 |
| 7 | 51.2 | 52.6 | 51.7 | 7 | 49.2 | 52.1 | 52.1 |
| 8 | 52.4 | 50.6 | 51.7 | 8 | 50.6 | 49.7 | 51.1 |
| 9 | 52.4 | 50.6 | 51.7 | 9 | 53 | 50.4 | 49.6 |
| 10 | 50.6 | 51.9 | 50.7 | 10 | 53 | 51.2 | 48.9 |
| 11 | 52.4 | 52.1 | 50.7 | 11 | 51.2 | 48.9 | 48.9 |
| Average | 51.3 | 51.5 | 51.2 | Average | 49.9 | 49.6 | 50.2 |
| SD value | 1 | 0.7 | 0.7 | SD value | 2 | 1.4 | 1.5 |

As shown in Table 1, no matter in the first array microfluidic chip or the second array microfluidic chip, there is a small difference in liquid volumes in different reaction wells. The standard deviation value between the reaction wells in the upper array, the standard deviation value between the reaction wells in the middle array, and the standard deviation value between the reaction wells in the lower array are small. Accordingly, it is shown that the array microfluidic chip of the present disclosure can transport the sample added to the sample loading well into each of the reaction wells quantitatively. Thus, the testing accuracy of the array microfluidic chip of the present disclosure can be enhanced significantly and has application potentials in related markets.

IV. The Array Microfluidic Chip of the Present Disclosure Applied to the Antibiotic Susceptibility Testing In the present experiment, the array microfluidic chip of the present disclosure is used to perform the antibiotic susceptibility testing on *Escherichia coli* ATCC25922 ("*E. coli* ATCC25922" hereafter) and *Staphylococcus aureus* ATCC29213 ("*S. aureus* ATCC29213" hereafter) to three antibiotics, namely Amikacin, Gentamicin and Vancomycin.

Figure 10A:
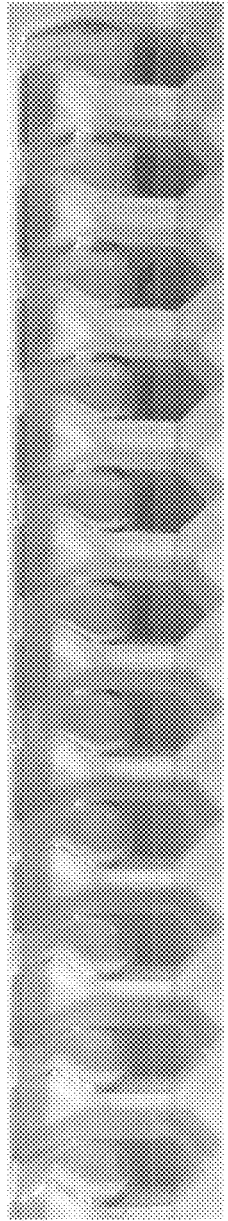
FIG. 10A shows a testing result of the array microfluidic chip of the present disclosure which is used to test the antibiotic susceptibility of *E. coli* ATCC25922 to Amikacin.
Figure 10B:
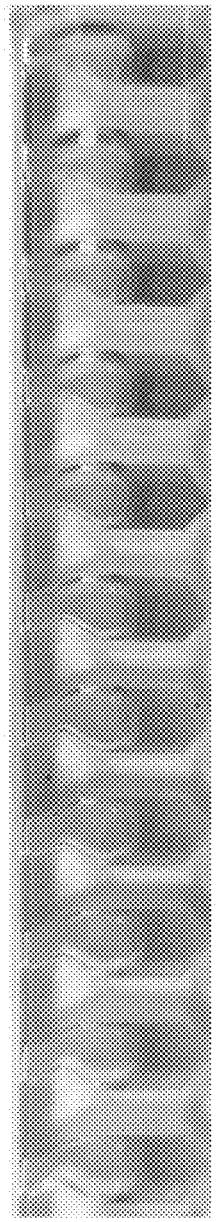
FIG. 10B shows a testing result of the array microfluidic chip of the present disclosure which is used to test the antibiotic susceptibility of *E. coli* ATCC25922 to Gentamicin.
Figure 10C:
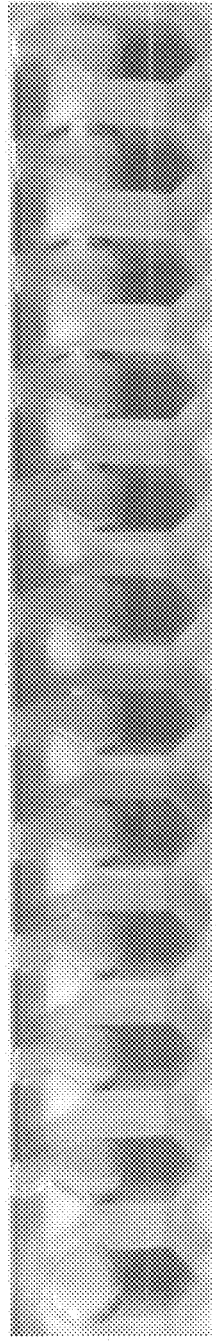
FIG. 10C shows a testing result of the array microfluidic chip of the present disclosure which is used to test the antibiotic susceptibility of *E. coli* ATCC25922 to Vancomycin.

In the experiment, the dried powders of Amikacin, Gentamicin or Vancomycin are respectively placed in different reaction wells of the array microfluidic chip with different Please refer to FIG. 10A, FIG. 10B, FIG. 10C and Table 2 simultaneously. FIG. 10A shows a testing result of the array microfluidic chip of the present disclosure which is used to test the antibiotic susceptibility of *E. coli* ATCC25922 to Amikacin, FIG. 10B shows a testing result of the array microfluidic chip of the present disclosure which is used to test the antibiotic susceptibility of *E. coli* ATCC25922 to Gentamicin, FIG. 10C shows a testing result of the array microfluidic chip of the present disclosure which is used to test the antibiotic susceptibility of *E. coli* ATCC25922 to Vancomycin, and Table 2 correspondingly shows the antibiotics concentrations and assessing results of different reaction wells arraying from left to right of each of FIG. 10A to FIG. 10C. Furthermore, in FIG. 10C, the far left one is the image of the independent well performed a negative control test, and it is noted that the testing result of the independent well is not shown in Table 2.

TABLE 2

| FIG. 10A - Amikacin | | | | | | | | | | | |
|---|---|---|---|---|---|---|---|---|---|---|---|
| Conc. (μg/mL) | 0 | 0.031 | 0.062 | 0.125 | 0.25 | 0.5 | 1 | 2 | 4 | 8 | 16 |
| Result | + | + | + | + | + | + | − | − | − | − | − |

TABLE 2-continued

| FIG. 10A - Amikacin | | | | | | | | | | | |
|---|---|---|---|---|---|---|---|---|---|---|---|
| Conc. (µg/mL) | 0 | 0.031 | 0.062 | 0.125 | 0.25 | 0.5 | 1 | 2 | 4 | 8 | 16 |
| FIG. 10B - Gentamicin | | | | | | | | | | | |
| Result | + | + | + | + | + | + | − | − | − | − | − |
| FIG. 10C - Vancomycin | | | | | | | | | | | |
| Result | + | + | + | + | + | + | + | + | + | + | + |

As shown in FIG. 10A to FIG. 10C, after culturing at 37° C. for 4 hours, the results of antibiotic susceptibility of *E. coli* ATCC25922 can be observed from the reaction wells of the array microfluidic chip. As shown in the results presented in Table 2, the minimum inhibitory concentration (MIC) of Amikacin to *E. coli* ATCC25922 is 1 µg/mL (the CLSI standard value thereof is MIC=0.5~4 µg/mL), the minimum inhibitory concentration of Gentamicin to *E. coli* ATCC25922 is 1 µg/mL (the CLSI standard value thereof is MIC=0.251 µg/mL), and the minimum inhibitory concentration of Vancomycin to *E. coli* ATCC25922 is larger than 16 µg/mL (the CLSI standard value thereof is MIC=R-resistance).

Figure 10D:
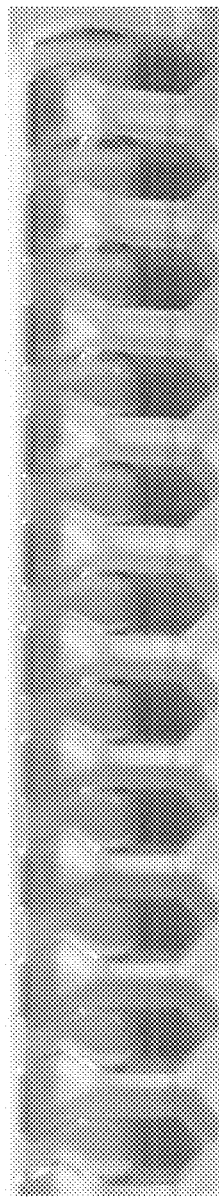
FIG. 10D shows a testing result of the array microfluidic chip of the present disclosure which is used to test the antibiotic susceptibility of *S. aureus* ATCC29213 to Amikacin.
Figure 10E:
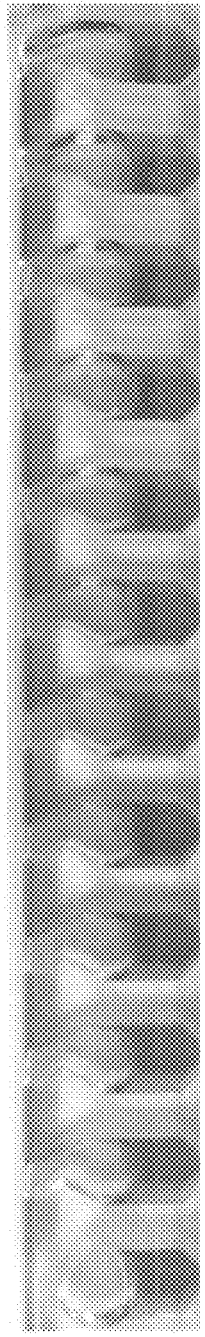
FIG. 10E shows a testing result of the array microfluidic chip of the present disclosure which is used to test the antibiotic susceptibility of *S. aureus* ATCC29213 to Gentamicin.
Figure 10F:
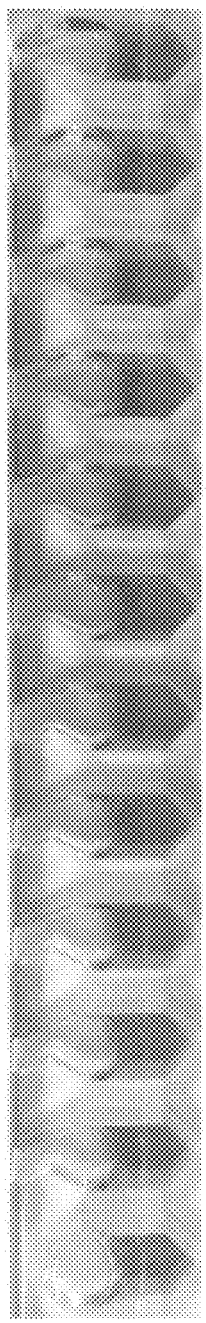
FIG. 10F shows a testing result of the array microfluidic chip of the present disclosure which is used to test the antibiotic susceptibility of *S. aureus* ATCC29213 to Vancomycin.

Furthermore, please refer to FIG. 10D, FIG. 10E, FIG. 10F and Table 3 simultaneously. FIG. 10D shows a testing result of the array microfluidic chip of the present disclosure which is used to test the antibiotic susceptibility of *S. aureus* ATCC29213 to Amikacin, FIG. 10E shows a testing result of the array microfluidic chip of the present disclosure which is used to test the antibiotic susceptibility of S. ATCC29213 to Gentamicin, FIG. 10F shows a testing result of the array microfluidic chip of the present disclosure which is used to test the antibiotic susceptibility of *S. aureus* ATCC29213 to Vancomycin, and Table 3 correspondingly shows the antibiotics concentrations and assessing results of different reaction wells arraying from left to right of each of FIG. 10D to FIG. 10F. Furthermore, in each of FIG. 10E and FIG. 10F, the far left one is the image of the independent well performed a negative control test, and it is noted that the testing result of the independent well is not shown in Table 3.

TABLE 3

| FIG. 10D - Amikacin | | | | | | | | | | | |
|---|---|---|---|---|---|---|---|---|---|---|---|
| Conc. (µg/mL) | 0 | 0.031 | 0.062 | 0.125 | 0.25 | 0.5 | 1 | 2 | 4 | 8 | 16 |
| Result | + | + | + | + | + | + | − | − | − | − | − |
| FIG. 10E - Gentamicin | | | | | | | | | | | |
| Result | + | + | + | + | − | − | − | − | − | − | − |
| FIG. 10F - Vancomycin | | | | | | | | | | | |
| Result | + | + | + | + | + | − | − | − | − | − | − |

As shown in FIG. 10D to FIG. 10F, after culturing at 37° C. for 5 hours and 30 minutes, the results of antibiotic susceptibility of *S. aureus* ATCC29213 can be observed from the reaction wells of the array microfluidic chip. As shown in the results presented in Table 3, the minimum inhibitory concentration of Amikacin to *S. aureus* ATCC29213 is 1 µg/mL (the CLSI standard value thereof is MIC=1~4 µg/mL), the minimum inhibitory concentration of Gentamicin to *S. aureus* ATCC29213 is 0.25 µg/mL (the CLSI standard value thereof is MIC=0.12~1 µg/mL), and the minimum inhibitory concentration of Vancomycin to *S. aureus* ATCC29213 is 0.5 µg/mL (the CLSI standard value thereof is MIC=0.5~2 µg/mL).

As shown in the aforementioned results, the method of antibiotic susceptibility testing of the present disclosure is performed by using the array microfluidic chip of the present disclosure, and the assessing results of antibiotic susceptibility obtained therefrom are consistent with those published by the Clinical & Laboratory Standards Institute (CLSI). Furthermore, the testing time of the method of antibiotic susceptibility testing of the present disclosure can be greatly shortened to 4 to 6 hours. Thus, the method of antibiotic susceptibility testing of the present disclosure has application potentials in related markets.

To sum up, by the arrangement of the plurality of reaction wells which are arranged in the array form, the resistance tests of different drugs and the microbial cultivation can be performed at the same time by the method of antibiotic susceptibility testing of the present disclosure, so that the antibiotic susceptibility testing can be performed rapidly by using the array microfluidic chip of the present disclosure under the premise that the mutual contaminations and interferences of reagents are prevented. Furthermore, by the arrangements that the plurality of air pores are respectively connected to one of the reaction wells and the reaction wells are connected to the vent space through the air pores, the samples added to sample loading well can be transported to each of the reaction wells quantitatively. Moreover, by the arrangement of the parallel flow channel with the width in proper, the liquid added to the sample loading well can fill in the area of the parallel flow channel between two of the reaction wells continuously after being transported to each of the reaction wells quantitatively. Further, when the chip mainbody is placed vertically, a gas-water isolation area will be formed between the reaction wells. Accordingly, it is favorable for preventing the cross-contamination caused by sample backflow between different reaction wells during operation. Thus, the testing accuracy of the array microfluidic chip of the present disclosure can be enhanced significantly and has application potentials in related markets.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. An array microfluidic chip, comprising:
   a chip mainbody, comprising:
      a sample loading well disposed on one side portion of the chip mainbody;
      a plurality of reaction wells respectively pipe-connected to the sample loading well, wherein the reaction wells are arranged in an array form; and
      an independent well disposed separately from the sample loading well;
   a transparent hydrophilic membrane disposed on the chip mainbody and covering the reaction wells, wherein the transparent hydrophilic membrane comprises:
      a plurality of air pores respectively connected to one of the reaction wells;

a first opening correspondingly connected to the sample loading well; and a second opening correspondingly connected to the independent well; and a covering sheet disposed on the transparent hydrophilic membrane and covering the air pores, wherein the covering sheet comprises:

an adhesive element disposed on one surface of the covering sheet and located between the covering sheet and the transparent hydrophilic membrane, wherein the adhesive element is arranged in a ring shape along an outer edge portion of the covering sheet; and a vent hole, wherein the covering sheet, the adhesive element and the transparent hydrophilic membrane are stacked to form a vent space, the vent space is connected to an external space of the array microfluidic chip through the vent hole, and the reaction wells are connected to the vent space through the air pores.

2. The array microfluidic chip of claim 1, wherein the chip mainbody further comprises a parallel flow channel, the sample loading well comprises a pipe-connected portion, and the pipe-connected portion is disposed on one side of the sample loading well away from the side portion of the chip mainbody, wherein the parallel flow channel is connected to the pipe-connected portion, and each of the reaction wells is connected to the parallel flow channel.

3. The array microfluidic chip of claim 2, wherein a width of the parallel flow channel ranges from 0.02 mm to 5.0 mm.

4. The array microfluidic chip of claim 2, wherein each of the reaction wells comprises:

a slanting chamber, wherein one end portion of the slanting chamber is connected to the parallel flow channel; and a reaction chamber connected to the other end portion of the slanting chamber.

5. The array microfluidic chip of claim 4, wherein an angle between a long axis of the slanting chamber and the parallel flow channel ranges from 90° to 179°.

6. The array microfluidic chip of claim 4, wherein a width of the slanting chamber of each of the reaction wells is larger than 0.1 mm.

7. The array microfluidic chip of claim 4, wherein the reaction chamber of each of the reaction wells comprises a bottom portion, and a shape of the bottom portion is arc shape or acute-angle shape.

8. The array microfluidic chip of claim 4, wherein each of the reaction wells corresponds to at least one of the air pores, and the at least one of the air pores corresponds to the reaction chamber of the one of the reaction wells.

9. The array microfluidic chip of claim 2, wherein the chip mainbody further comprises at least one slanting flow channel, and a number of the parallel flow channel is at least two, the slanting flow channel is connected between one of the parallel flow channels and the pipe-connected portion, and the one of the parallel flow channels is connected to the sample loading well through the slanting flow channel.

10. The array microfluidic chip of claim 1, wherein the chip mainbody comprises at least three of the reaction wells.

11. The array microfluidic chip of claim 1, wherein a surface close to the transparent hydrophilic membrane of the chip mainbody comprises an adhesive layer.

12. The array microfluidic chip of claim 1, wherein a diameter of each of the air pores ranges from 0.01 mm to 5 mm.

13. The array microfluidic chip of claim 1, wherein the chip mainbody, the transparent hydrophilic membrane and the covering sheet are made of a plastic material.

14. A method of antibiotic susceptibility testing, comprising;

providing the array microfluidic chip of claim 1, wherein the array microfluidic chip is placed on an operating platform, and the reaction wells of the chip mainbody respectively store an antibiotic solution or a dried antibiotic powder;

performing a bacterial solution adding step, wherein the array microfluidic chip is placed tilted against the operating platform so as to make the side portion of the chip mainbody away from the operating platform, a bacteria-containing medium is added to the sample loading well from the first opening, and then the bacteria-containing medium is transported to each of the reaction wells from the sample loading well quantitatively;

performing a sealing step, wherein the first opening and the vent hole are sealed so as to isolate the sample loading well and the reaction wells from the external space of the array microfluidic chip;

performing a mixing step, wherein a relative position of the array microfluidic chip and the operating platform is adjusted so as to fully mix the bacteria-containing medium and the antibiotic solution or the dried antibiotic powder of each of the reaction wells and then form a reaction solution; and performing a reacting step, wherein the reaction solution is reacted for a predetermined reaction time so as to obtain a reaction result.

15. The method of antibiotic susceptibility testing of claim 14, wherein a height of the side portion of the chip main body away from the operating platform is H, and the following condition is satisfied:

$H \geq 1$ cm.

16. The method of antibiotic susceptibility testing of claim 14, wherein each of the reaction wells comprises a slanting chamber and a reaction chamber, the reaction chamber stores the antibiotic solution or the dried antibiotic powder, and the bacteria-containing medium is transported to the slanting chamber of each of the reaction wells from the sample loading well and then mixed with the antibiotic solution or the dried antibiotic powder of the reaction wells.

17. The method of antibiotic susceptibility testing of claim 14, wherein in the bacterial solution adding step, a bacteria-free medium is further added to the independent well from the second opening.

18. The method of antibiotic susceptibility testing of claim 17, wherein in the sealing step, the second opening is further sealed so as to isolate the independent well from the external space of the array microfluidic chip.

* * * * *